(12) United States Patent
Kim et al.

(10) Patent No.: US 12,351,551 B2
(45) Date of Patent: Jul. 8, 2025

(54) METHOD FOR PRODUCING MAXACALCITOL, AND INTERMEDIATE THEREFOR

(71) Applicant: YONSUNG FINE CHEMICAL CO., LTD., Hwaseong-si (KR)

(72) Inventors: Seung Woo Kim, Suwon-si (KR); Se Gyo Jung, Hwaseong-si (KR); In A Jung, Yongin-si (KR); Hyunik Shin, Suwon-si (KR)

(73) Assignee: YONSUNG FINE CHEMICAL CO., LTD., Hwaseong-si (KR)

( * ) Notice: Subject to any disclaimer, the term of this patent is extended or adjusted under 35 U.S.C. 154(b) by 532 days.

(21) Appl. No.: 17/780,344

(22) PCT Filed: Nov. 26, 2020

(86) PCT No.: PCT/KR2020/016987
§ 371 (c)(1),
(2) Date: May 26, 2022

(87) PCT Pub. No.: WO2021/107646
PCT Pub. Date: Jun. 3, 2021

(65) Prior Publication Data
US 2023/0065886 A1 Mar. 2, 2023

(30) Foreign Application Priority Data
Nov. 27, 2019 (KR) .................. 10-2019-0154626

(51) Int. Cl.
*C07C 401/00* (2006.01)
(52) U.S. Cl.
CPC .................. *C07C 401/00* (2013.01)
(58) Field of Classification Search
CPC .................. C07D 401/00; C07F 7/1804
See application file for complete search history.

(56) References Cited

U.S. PATENT DOCUMENTS

| 5,436,401 A | 7/1995 | Kato et al. |
| 9,221,753 B2 * | 12/2015 | Kashiwagi ............. A61P 37/02 |
| 2010/0217020 A1 | 8/2010 | Ogasawara et al. |
| 2016/0237030 A1 * | 8/2016 | Zheng ................. C07D 303/22 |

FOREIGN PATENT DOCUMENTS

| CN | 104496871 A | 4/2015 |
| EP | 0 078 704 A1 | 5/1983 |
| KR | 10-1998-0701671 A | 6/1998 |
| KR | 10-2000-0010702 A | 2/2000 |
| KR | 10-2010-0099181 A | 9/2010 |
| WO | 2012/122451 A2 | 9/2012 |

OTHER PUBLICATIONS

Yagamare Fall, "A New Approach to the Synthesis of the 25-Hydroxy-22-Oxa-Vitamin $D_3$ Side Chain", Tetrahedron Letters, 1997, pp. 4909-4912, vol. 38, No. 27.
International Search Report for PCT/KR2020/016987 dated Mar. 11, 2021 [PCT/ISA/210].
Monsalve et al., "An efficient enzymatic preparation of 20-pregnane succinates: chemoenzymatic synthesis of 20b-hemisuccinyloxy-5aH-pregnan-3-one", Tetrahedron 64 (2008) 1721-1730.
Krow, "The Baeyer-Villiger Oxidation of Ketones and Aldehydes", Organic Reactions, vol. 43, 1993, 4 pages.
Gool et al., "Synthesis of 14,20-Bis-epi-1a,25-dihydroxy-19-norvitamin D3 and Analogues", Eur. J. Org. Chem. 1999, 2241-2248.

* cited by examiner

*Primary Examiner* — Joseph K McKane
*Assistant Examiner* — Karen Cheng
(74) *Attorney, Agent, or Firm* — Sughrue Mion, PLLC

(57) ABSTRACT

A new and improved method for preparing maxacalcitol and an intermediate therefor is provided. The method is an efficient and cost-effective process for preparing maxacalcitol and an intermediate therefor.

10 Claims, No Drawings

METHOD FOR PRODUCING MAXACALCITOL, AND INTERMEDIATE THEREFOR

CROSS REFERENCE TO RELATED APPLICATIONS

This application is a National Stage of International Application No. PCT/KR2020/016987 filed Nov. 26, 2020, claiming priority based on Korean Patent Application No. 10-2019-0154626 filed Nov. 27, 2019.

TECHNICAL FIELD

The present invention relates to a process for preparing maxacalcitol and an intermediate therefor. More particularly, the present invention relates to an efficient and cost-effective process for preparing maxacalcitol, and an intermediate therefor.

BACKGROUND ART

Maxacalcitol of the following formula (1) ((1R,3S,Z)-5-(2-((1 S,3aS,7aS,E)-1-((5)-1-(3-hydroxy-3-methylbutoxy)ethyl)-7a-methyloctahydro-4H-inden-4-ylidene)ethylidene)-4-methylenecyclohexane-1,3-diol) is an active ingredient of OXAROL®, which is a medicine developed by Chugai Pharmaceutical in Japan and used as an ointment to treat skin diseases such as psoriasis or an injection to treat secondary hyperthyroidism.

(1)

U.S. Pat. No. 5,436,401 discloses a process for preparing maxacalcitol. The patent describes a process for preparing maxacalcitol by light irradiation and thermal isomerization using DHEA as a starting material, as shown in the following reaction scheme 1. However, the preparation process has problems that it is very difficult to supply starting materials to be obtained from microorganisms and it is not suitable for mass production.

[Reaction Scheme 1]

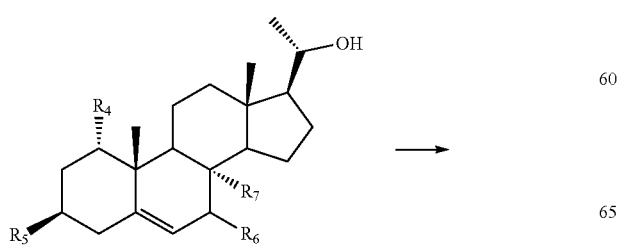

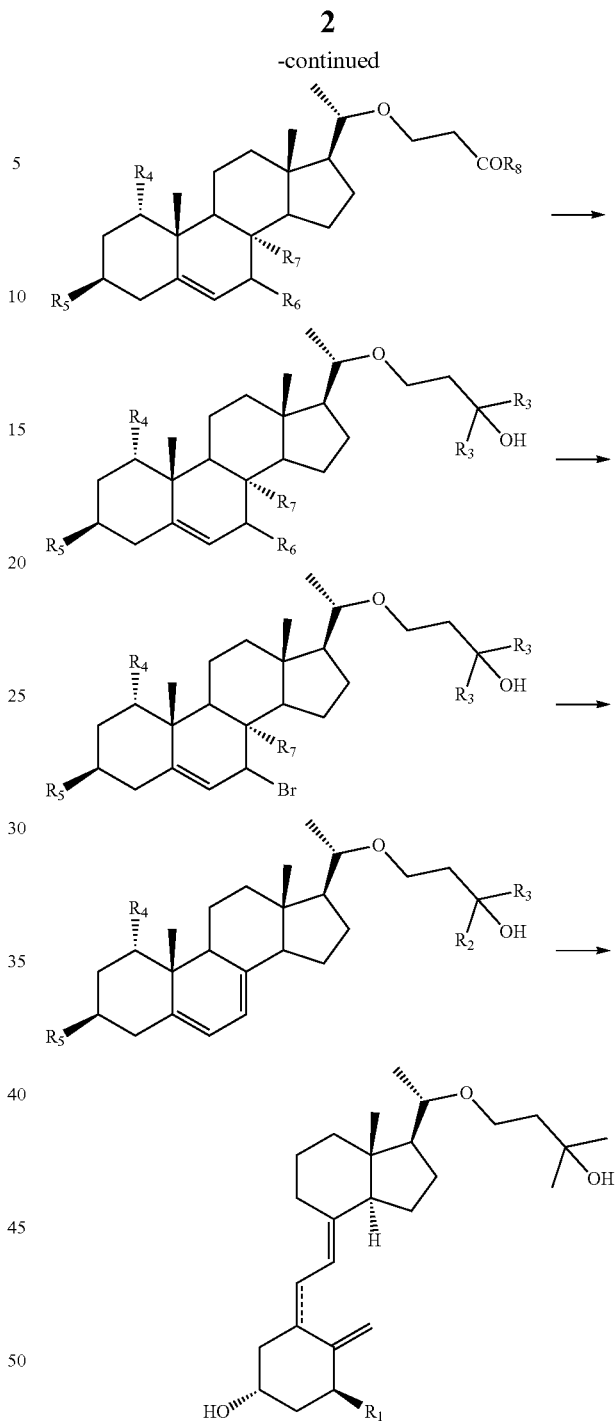

Further, literature [*Tetrahedron Letters*, 1997, 38(27), 4909-4912] describes a process for preparing a key intermediate of maxacalcitol by Michael addition, hydrogenation and alkylation, as shown in the following reaction scheme 2.

[Reaction Scheme 2]

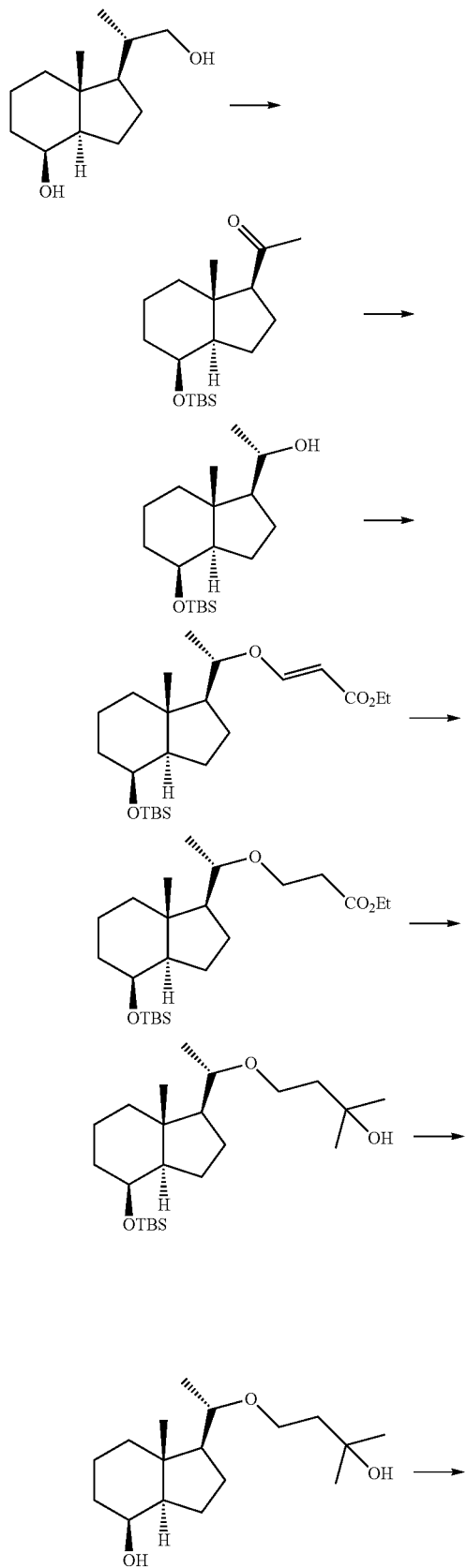

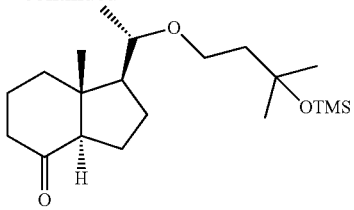

However, the prior preparation process has a problem that it is not suitable for mass production due to multiple steps and certain conditions.

DISCLOSURE

Technical Problem

The inventors have endeavored to solve the above problems in the preparation of maxacalcitol, and found that the compound of formula (5), which is a key intermediate of maxacalcitol, can be simply prepared using the compound of formula (2) as a starting material, and maxacalcitol can be efficiently and cost-effectively prepared using the same.

Accordingly, it is an object of the present invention to provide a process for preparing an intermediate used for preparing maxacalcitol.

It is another object of the present invention to provide an intermediate prepared by the above process.

It is still another object of the present invention to provide a process for preparing maxacalcitol using the above intermediate.

Technical Solution

One embodiment of the present invention relates to a process for preparing a compound of the following formula (5), which comprises the steps of:

(i) subjecting a compound of the following formula (2) to ozonolysis and reduction to obtain a compound of the following formula (3);

(ii) subjecting the compound of the following formula (3) to Baeyer-Villiger oxidation to obtain a compound of the following formula (4); and (iii) subjecting the compound of the following formula (4) to Homer-Wadsworth-Emmons reaction with a compound of the following formula (6):

(5)

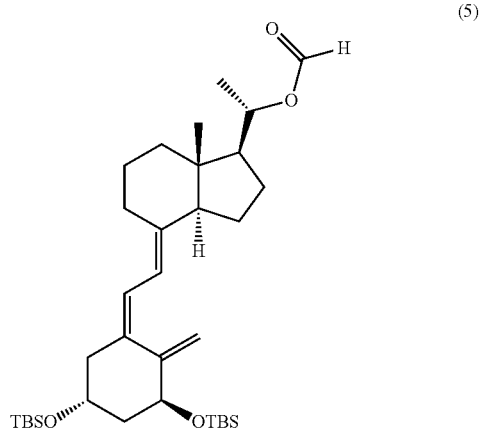 [SMILES: C=C1/C(=C\C=C2/CCC[C@]3(C)[C@@H]([C@H](C)OC=O)CC[C@@H]23)C[C@@H](O[Si](C)(C)C(C)(C)C)C[C@@H]1O[Si](C)(C)C(C)(C)C]

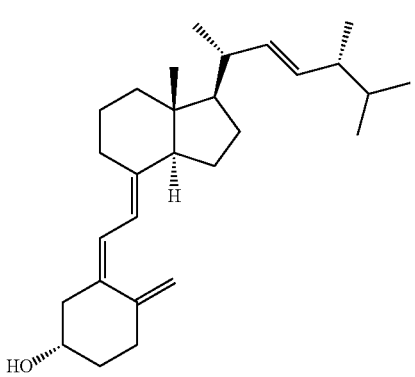
(2)

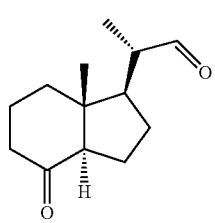
(3)

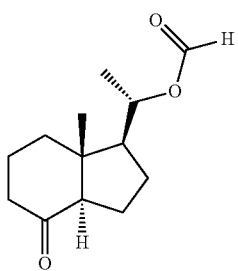
(4)

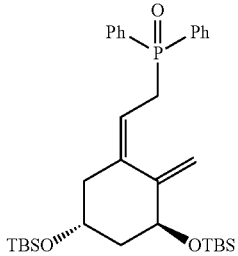
(6)

wherein,
TBS is t-butyldimethylsilyl, and
Ph is phenyl.

One embodiment of the present invention relates to a compound of the following formula (5), which is an intermediate for the preparation of maxacalcitol.

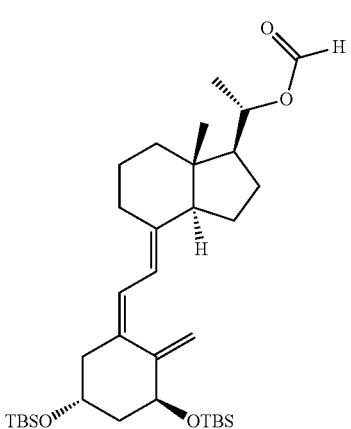
(5)

One embodiment of the present invention relates to a process for preparing maxacalcitol of the following formula (1), which comprises the steps of:
(vi) subjecting a formate group of a compound of the following formula (5) to hydrolysis to obtain a compound of the following formula (7);
(v) subjecting the compound of the following formula (7) to nucleophilic substitution with a compound of the following formula (8) to obtain a compound of the following formula (9);
(vi) subjecting an epoxide group of the compound of the following formula (9) to ring-opening reduction to obtain a compound of the following formula (10); and
(vii) deprotecting a t-butyldimethylsilyl protecting group of the compound of the following formula (10):

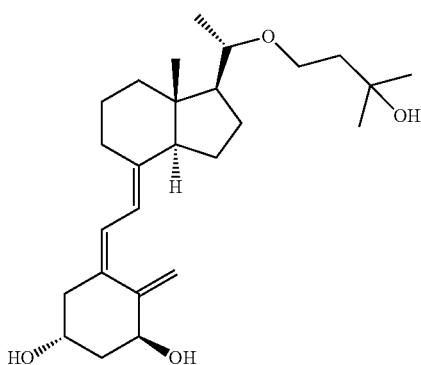
(1)

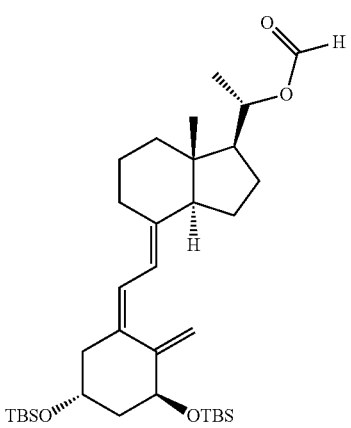
(5)

-continued

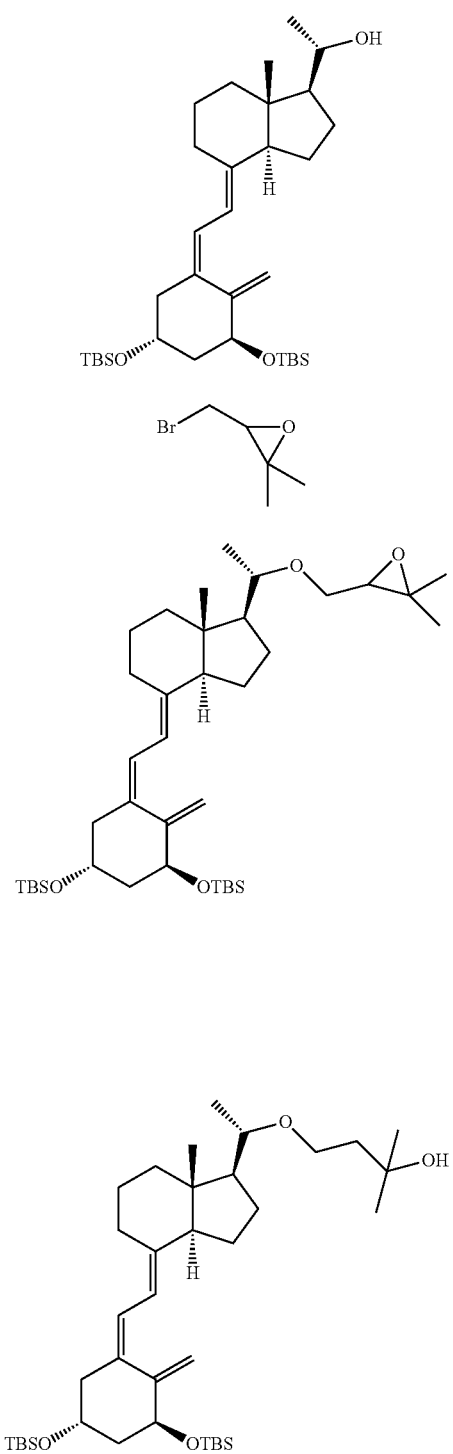

wherein,
TBS is t-butyldimethylsilyl.

Hereinafter, the preparation process of the present invention is described in more detail referring to the following reaction scheme 3. The process depicted in the following reaction scheme 3 represents merely a typical example, and various changes may be made to reagents and reaction conditions without limitation.

[Reaction Scheme 3]

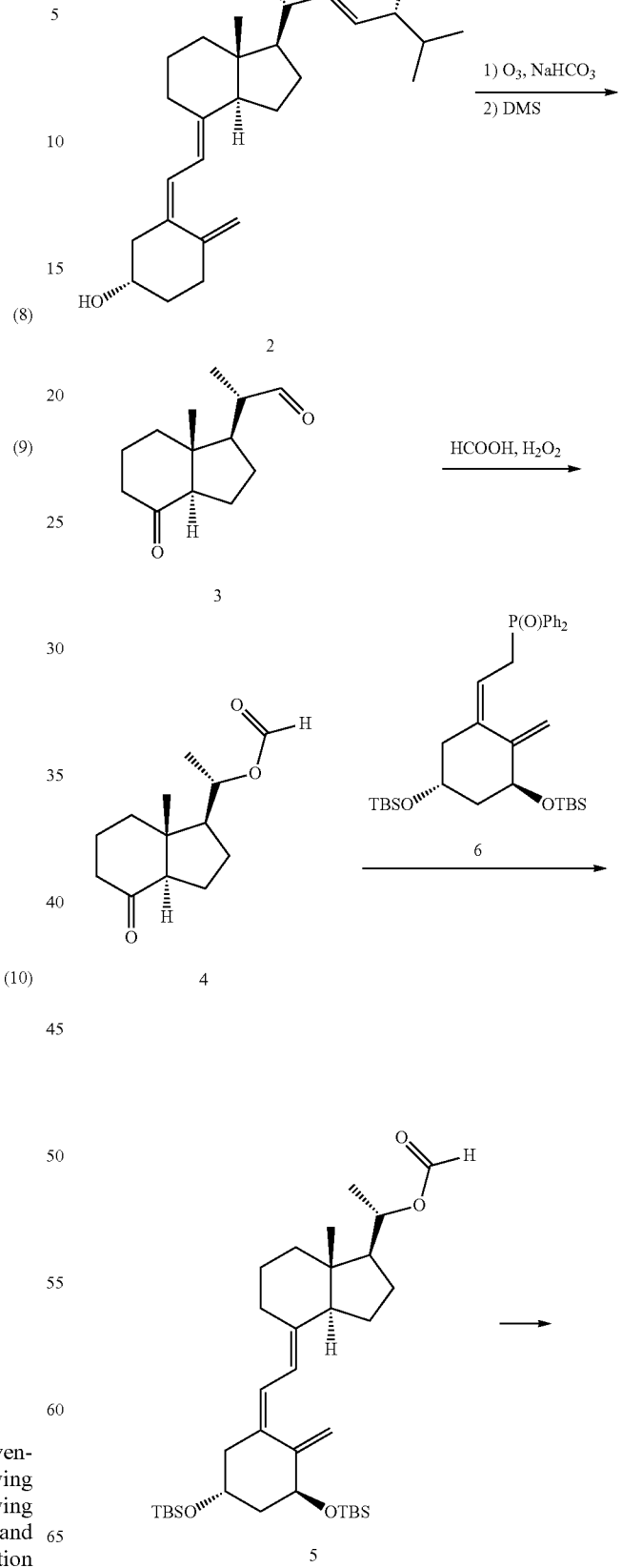

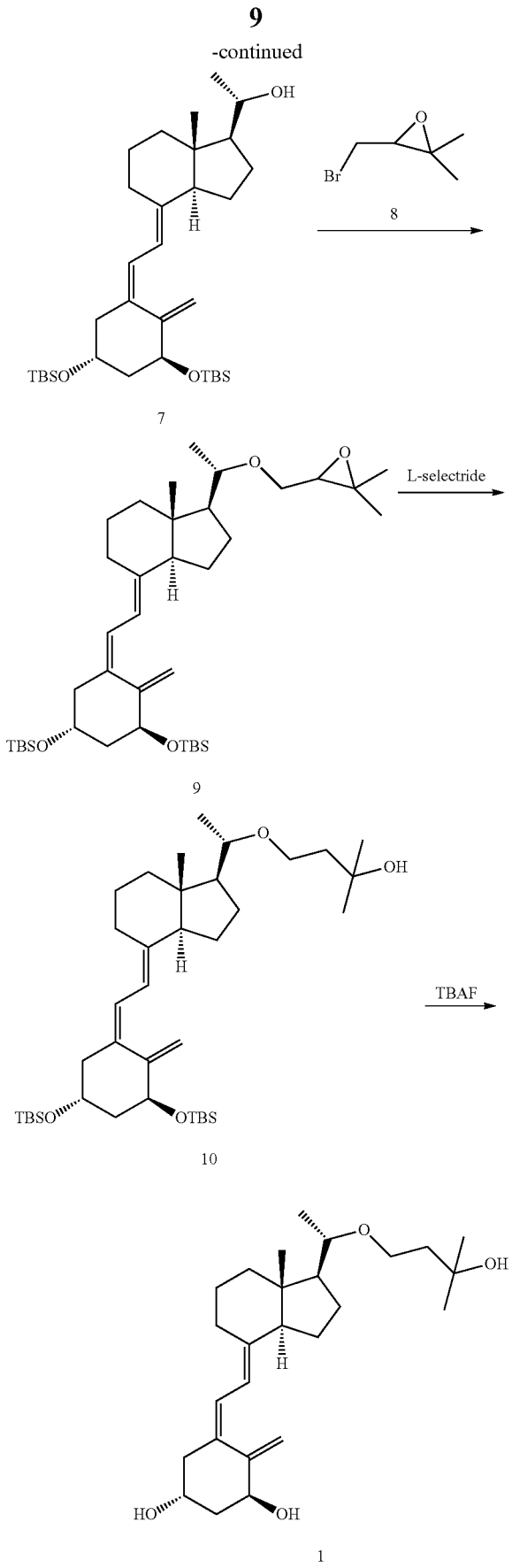

Step 1: Synthesis of Compound of Formula (3)

The compound of formula (3) can be prepared by subjecting the compound of formula (2) to ozonolysis and reduction.

The ozonolysis can be carried out using ozone. Particularly, it is preferred to use an industrial ozone generator.

Further, the ozonolysis is preferably carried out in the presence of a base such as sodium bicarbonate.

As the reaction solvent, a mixed solvent of polar and non-polar is suitable. Particularly, a mixed solvent of dichloromethane and methanol is preferred.

The reaction temperature is suitably −60 to −70° C., and termination of the ozonolysis is preferably carried out according to the saturation degree of ozone in the resulting solution, which can be confirmed with the naked eye.

The reduction may be carried out in the presence of a reductant. As the reductant, triphenylphosphine, thiourea, zinc, dimethylsulfide, etc. may be used. Particularly, dimethylsulfide is preferred.

The reaction temperature is suitably 20 to 30° C., and the reaction time is preferably 12 to 16 hours.

Meanwhile, the compound of formula (2) used as a starting material may be obtained commercially or prepared easily by means known in the art.

Step 2: Synthesis of Compound of Formula (4)

The compound of formula (4) can be prepared by subjecting the compound of formula (3) to Baeyer-Villiger oxidation.

The Baeyer-Villiger oxidation may be carried out using meta-chloroperoxybenzoic acid, performic acid, hydrogen peroxide, peracetic acid, etc. Particularly, performic acid is preferred.

As the reaction solvent, a non-polar solvent is suitable, and dichloromethane, chloroform, etc. may be used. Particularly, dichloromethane is preferred.

The reaction temperature is suitably 20 to 30° C., and the reaction time is preferably 16 to 24 hours.

Step 3: Synthesis of Compound of Formula (5)

The compound of formula (5) can be prepared by subjecting the compound of formula (4) to Horner-Wadsworth-Emmons reaction with the compound of formula (6).

The Horner-Wadsworth-Emmons reaction can be carried out in presence of a base.

As the base, n-butyllithium, sodium hydride, methyl magnesium bromide, lithium bis(trimethylsilyl)amide, isopropyl magnesium bromide, sodium carbonate, etc. may be used. Particularly, n-butyllithium is preferred.

As the reaction solvent, tetrahydrofuran, hexane and diethylether may be used. Particularly, tetrahydrofuran is preferred.

The reaction temperature is suitably −60 to −50° C., and the reaction time is preferably 1 to 2 hours.

Step 4: Synthesis of Compound of Formula (7)

The compound of formula (7) can be prepared by subjecting the formate group of the compound of formula (5) to hydrolysis.

The hydrolysis can be carried out in the presence of a base.

As the base, sodium methoxide, potassium methoxide, sodium carbonate, potassium carbonate, n-butyllithium, diisobutylaluminium hydride, etc. may be used. Particularly, sodium methoxide or potassium carbonate is preferred.

As the reaction solvent, methanol, ethanol, tetrahydrofuran, water, etc. may be used. Particularly, a mixed solvent of methanol and tetrahydrofuran is preferred.

The reaction temperature is suitably 15 to 25° C., and the reaction time is preferably 2 to 4 hours.

Step 5: Synthesis of Compound of Formula (9)

The compound of formula (9) can be prepared by subjecting the compound of formula (7) to nucleophilic substitution with the compound of formula (8).

The nucleophilic substitution can be carried out in the presence of a base.

As the base, sodium hydride, potassium carbonate, lithium bis(trimethylsilyl)amide, etc. may be used. Particularly, sodium hydride is preferred.

As the reaction solvent, tetrahydrofuran, diethylether, etc. may be used. Particularly, tetrahydrofuran is preferred.

The reaction temperature is suitably 60 to 70° C., and the reaction time is preferably 1 to 2 hours.

Step 6: Synthesis of Compound of Formula (10)

The compound of formula (10) can be prepared by subjecting the epoxide group of the compound of formula (9) to ring-opening reduction.

The ring-opening reduction can be carried out in the presence of a reductant.

As the reductant, L-selectride, N-selectride, K-selectride, aluminium hydride, diisobutylaluminium hydride, sodium borohydride, etc. may be used. Particularly, L-selectride is preferred.

As the reaction solvent, tetrahydrofuran, diethylether, methanol, ethanol, etc. may be used. Particularly, tetrahydrofuran is preferred.

The reaction temperature is suitably 60 to 70° C., and the reaction time is preferably 2 to 3 hours.

Step 7: Synthesis of Compound of Formula (1)

The compound of formula (1) can be prepared by deprotecting the t-butyldimethylsilyl protecting group of the compound of formula (10).

The deprotection can be carried out in the presence of an acid catalyst or a fluoride compound.

As the acid catalyst, camphorsulfonic acid, methanesulfonic acid, p-toluenesulfonic acid, etc. may be used. As the fluoride compound, tetra-n-butylammonium fluoride, potassium fluoride, etc. may be used. Particularly, tetra-n-butylammonium fluoride is preferred.

As the reaction solvent, tetrahydrofuran, dimethylsulfoxide, dimethylformamide, etc. may be used. Particularly, tetrahydrofuran is preferred.

The reaction temperature is suitably 15 to 25° C., and the reaction time is preferably 70 to 75 hours.

Advantageous Effects

In accordance with the preparation process of the present invention, the compound of formula (5), which is a key intermediate for the preparation of maxacalcitol, can be efficiently and simply prepared, and maxacalcitol can be efficiently and cost-effectively prepared therefrom.

BEST MODE

The present invention will be described in more detail by following examples. It will be obvious to those skilled in the art that these examples are merely described for illustration of the present invention and the scope of the present invention is not limited thereto.

Example 1: Preparation of Compound of Formula (3)

The compound of formula (2) (50.000 g, 126.05 mmol) and sodium bicarbonate (0.741 g, 8.82 mmol) were dissolved in dichloromethane (1.500 L, 30 v/w) and methanol (0.500 L, 10 v/w), followed by stirring in an acetone-dry ice bath. When the temperature of the resulting solution reached −70° C., an ozone generator was operated. When the resulting solution turned completely blue after stirring for 6 hours, the ozone generator was stopped. Argon was injected for 3 hours while stirring until the resulting solution became transparent to remove the supersaturated ozone in the resulting solution. When the temperature of the resulting solution reached −30° C. after removing the acetone-dry ice bath, dimethylsulfide (0.046 L, 630.26 mmol) was added thereto. After stirring at 20° C. for 16 hours, the resulting solution was concentrated to remove dichloromethane and methanol. Dichloromethane (0.500 L, 10 v/w) and water (0.750 L, 15 v/w) were added to the concentrated residue. A work-up process was performed by adding sodium sulfite (79.44 g, 630.26 mmol) to the solution having separated layers, followed by stirring for 2 hours. The separated organic layer was dried over sodium sulfate, followed by filtration and concentration. The concentrated residue weighed 33.60 g, and the compound of formula (3) containing impurities was used to prepare the compound of formula (4) without further purification.

$^1$H NMR (300 MHz, CDCl$_3$) δ9.61 (d, 1H, J=2.9 Hz), 2.49 (dd, 1H, J=7.6 Hz, 11.6 Hz), 2.43-2.35 (m, 1H), 2.34-2.25 (m, 2H), 2.11-1.74 (m, 7H), 1.51-1.35 (m, 1H), 1.17 (d, 3H, J=6.9 Hz), 0.95 (dd, 1H, J=6.8 Hz, 10.7 Hz), 0.69 (s, 3H); $^{13}$C NMR (75 MHz, CDCl$_3$) δ 211.2, 204.2, 61.0, 51.4, 50.0, 49.1, 40.9, 38.6, 26.4, 23.9, 19.5, 13.4, 12.8.

Example 2: Preparation of Compound of Formula (4)

The concentrated residue (33.6 g) containing the compound of formula (3) obtained from Example 1 was dissolved in dichloromethane (151.2 mL, 4.5 v/w), followed by stirring in an ice bath. When the temperature of the resulting solution reached 0 to 4° C., formic acid (126.0 mL, 3.75 v/w) was added thereto. And then, 30% of hydrogen peroxide solution (69.3 mL, 2.06 v/w) was slowly added dropwise thereto for 30 minutes. After removing the ice bath and stirring at 20° C. for 16 hours, dichloromethane (120 mL) was added to dilute the reaction solution, and the organic layer separated from the aqueous layer was obtained. The separated organic layer was washed once with 30% of sodium thiosulfate aqueous solution (300 mL) and once with 7% of sodium bicarbonate aqueous solution (300 mL). The organic layer was separated and dried over sodium sulfate, followed by filtration and concentration. The concentrated residue was purified by column chromatography (hexane:ethyl acetate=10:1) to give the compound of formula (4) (13.52 g, 47.8% from the compound of formula (2)).

$^1$H NMR (300 MHz, CDCl$_3$) δ 8.02 (s, 1H), 5.13-5.04 (m, 1H), 2.49 (dd, 1H, J=7.5 Hz, 11.4 Hz), 2.35-2.17 (m, 2H), 2.09-1.71 (m, 7H), 1.66-1.49 (m, 2H), 1.31 (d, 3H, J=6.3 Hz), 0.66 (s, 3H); $^{13}$C NMR (75 MHz, CDCl$_3$) δ 210.9, 160.6, 71.8, 61.5, 55.6, 48.8, 40.8, 37.8, 24.5, 23.6, 20.6, 19.0, 13.1.

Example 3: Preparation of Compound of Formula (5)

The compound of formula (6) (42.88 g, 73.6 mmol) in which the solvent was completely dried was dissolved in tetrahydrofuran (225.0 mL, 15 v/w), followed by stirring. While the temperature of the resulting solution was maintained at −45 to −40° C. under argon gas, 2.5 M of n-butyllithium hexane solution (38.4 mL, 15.4 mmol) was slowly added dropwise thereto for 1 hour, followed by stirring at −45 to −40° C. for 1 hour. While the temperature of the resulting solution was maintained at −75 to −70° C., a solution of the compound of formula (4) (15.00 g, 66.9 mmol) dissolved in tetrahydrofuran (30.0 mL, 2 v/w) was slowly added dropwise thereto for 1 hour, followed by stirring at the same temperature for 30 minutes. After warming to 0 to 5° C. slowly for 30 minutes, water (150.0 mL, 10 v/w) was added dropwise thereto for 10 minutes maintaining the same temperature. The resulting solution was warmed to 20° C. slowly for 30 minutes, followed by stirring at the same temperature for 30 minutes. After ethyl acetate (500.0 mL) was added to dilute the reactants, the organic layer was washed with water (500.0 mL), and combined organic layer was dried over sodium sulfate, followed by filtration and concentration. The concentrated residue was purified by column chromatography (hexane:ethyl acetate=30:1) to give the compound of formula (5) (16.54 g, 42%), which can be used to prepare the compound of formula (7) without purification.

$^1$H NMR (300 MHz, CDCl$_3$) δ8.26 (s, 1H), 6.23 (d, 1H, J=11.2 Hz), 6.03 (d, 1H, J=11.3 Hz), 5.18 (d, 1H, J=1.4 Hz), 5.11-5.04 (m, 1H), 4.85 (d, 1H, J=2.4 Hz), 4.37 (dd, 1H, J=3.8 Hz, 6.5 Hz), 4.23-4.15 (m, 1H), 2.85 (dd, 1H, J=3.8 Hz, 14.4 Hz), 2.45 (dd, 1H, J=3.7 Hz, 13.1 Hz), 2.21 (dd, 1H, J=7.4 Hz, 13.0 Hz), 1.90-1.65 (m, 8H), 1.55-1.50 (m, 4H), 1.36-1.19 (m, 5H), 0.87 (s, 18H), 0.55 (s, 3H), 0.06 (s, 12H); $^{13}$C NMR (75 MHz, CDCl$_3$) δ 160.8, 148.3, 139.7, 135.6, 122.9, 118.5, 111.3, 73.3, 72.1, 67.5, 56.1, 55.6, 46.1, 44.8, 39.6, 28.7, 25.9, 25.8, 25.1, 23.1, 22.0, 20.8, 18.2, 18.1, 12.5, −4.7, −4.8, −5.1.

Example 4: Preparation of Compound of Formula (7)

The compound of formula (5) (30.00 g, 50.9 mmol) obtained from Example 3 was dissolved in methanol (180.0 mL, 6 v/w) and tetrahydrofuran (30.0 mL, 1 v/w), and potassium carbonate (1.41 g, 10.2 mmol) was added thereto. The resulting solution was stirred at 20 to 25° C. for 4 hours, followed by distilling under reduced pressure to remove 150 to 200 mL of the solvent. Water (300.0 mL) and ethyl acetate (300.0 mL) were added to the concentrated reactants, followed by enough mixing to obtain the organic layer. The organic layer was dried over sodium sulfate, followed by filtration and concentration. The concentrated residue was purified by column chromatography (hexane:ethyl acetate=20:1) to give the compound of formula (7) (27.88 g, 98%).

$^1$H NMR (300 MHz, CDCl$_3$) δ 6.22 (d, 1H, J=11.2 Hz), 6.03 (d, 1H, J=11.3 Hz), 5.18 (dd, 1H, J=1.0 Hz, 2.4 Hz), 4.86 (d, 1H, J=2.3 Hz), 4.37 (dd, 1H, J=3.8 Hz, 6.6 Hz), 4.22-4.15 (m, 1H), 3.73-3.69 (m, 1H), 2.83 (dd, 2H, J=3.8 Hz, 11.3 Hz), 2.44 (dd, 1H, J=3.8 Hz, 13.1 Hz), 2.21 (dd, 1H, J=7.3 Hz, 13.1 Hz), 2.04-1.1.75 (m, 5H), 1.75-1.43 (m, 7H), 1.33-1.22 (m, 5H), 0.87 (m, 18H), 0.53 (s, 3H), 0.06 (m, 12H); $^{13}$C NMR (75 MHz, CDCl$_3$) δ 148.3, 140.2, 135.4, 123.0, 118.3, 111.2, 72.0, 70.3, 67.5, 58.7, 56.1, 46.0, 44.8, 39.6, 28.7, 25.9, 25.8, 24.9, 23.6, 23.1, 22.1, 18.25, 18.16, 12.6, −4.65, −4.68, −4.8, −5.1.

Example 5: Preparation of Compound of Formula (9)

The compound of formula (7) (31.87 g, 56.87 mmol) in which the solvent was completely dried was dissolved in tetrahydrofuran (49.1 mL, 1.54 v/w), and 60% w/w of sodium hydride (5.69 g, 142.17 mmol) was added thereto, followed by stirring at 20 to 25° C. for 30 minutes. The compound of formula (8) (18.20 g, 113.74 mmol) was added to the resulting solution, followed by heating to 65 to 70° C. and stirring for 1 hour. 10% of ammonium chloride aqueous solution (100 mL, 3.14 v/w) was slowly added dropwise thereto at 0 to 5° C. for 30 minutes, followed by extracting twice using ethyl acetate (100 mL, 3.14 v/w). The obtained organic layer was dried over sodium sulfate, followed by filtration and concentration. The residue was purified by column chromatography (hexane:ethyl acetate=49:1) to give the compound of formula (9) (31.76 g, 87%).

1H NMR (300 MHz, CDCl$_3$) δ 6.23 (d, 1H, J=11.2 Hz), 6.03 (d, 1H, J=11.2 Hz), 5.19 (d, 1H, J=1.5 Hz), 4.86 (d, 1H, J=2.4 Hz), 4.38 (dd, 1H, J=3.9 Hz, 6.6 Hz), 4.21-4.18 (m, 1H), 3.66 (ddd, 1H, J=2.3 Hz, 5.5 Hz, 10.8 Hz), 3.45-3.23 (m, 2H), 2.92 (dt, 1H, J=1.9 Hz, 5.4 Hz), 2.83 (dd, 1H, J=3.3 Hz, 11.9 Hz), 2.44 (dd, 1H, J=3.7 Hz, 13.1 Hz), 2.21 (dd, 1H, J=7.2 Hz, 13.1 Hz), 2.08-1.94 (m, 2H), 1.94-1.77 (m, 3H), 1.77-1.60 (m, 3H), 1.58-1.41 (m, 4H), 1.38-1.25 (m, 8H), 1.23-1.11 (m, 3H), 0.88-0.87 (m, 18H), 0.53-0.52 (m, 3H), 0.07-0.06 (m, 12H).

Example 6: Preparation of Compound of Formula (10)

The compound of formula (9) (31.66 g, 49.07 mmol) in which the solvent was completely dried was dissolved in tetrahydrofuran (126.6 mL, 4 v/w) under argon gas, and 1M of L-selectride tetrahydrofuran solution (88.3 mL, 88.33 mmol) was added dropwise thereto at 20 to 25° C. for 30 minutes. The resulting solution was heated to 65 to 70° C. while stirring for 2 hours, and 10% of sodium hydroxide aqueous solution (70 mL, 2.21 v/w) was added dropwise thereto for 30 minutes while maintaining 0 to 5° C. And then, 30% of hydrogen peroxide solution (31.7 mL, 1 v/w) was added dropwise thereto for 30 minutes. After the resulting solution was stirred at 20 to 25° C. for 1 hour, 30% of sodium thiosulfate aqueous solution (100 mL, 3.16 v/w) was added thereto at the same temperature, followed by stirring at 20 to 25° C. for 1 hour. Ethyl acetate (100 mL, 3.16 v/w) was added to the resulting solution for extraction, and then ethyl acetate (200 mL, 6.32 v/w) was added to the aqueous layer to extract once. Afterwards, the combined organic layer was dried over sodium sulfate, followed by filtration and concentration. The residue was purified by column chromatography (hexane:ethyl acetate=19:1) to give the compound of formula (10) (29.85 g, 94%).

$^1$H NMR (300 MHz, CDCl$_3$) δ 6.22 (d, 1H, J=11.2 Hz), 6.02 (d, 1H, J=11.2 Hz), 5.19 (d, 1H, J=1.4 Hz), 4.86 (d, 1H, J=2.3 Hz), 4.38 (dd, 1H, J=4.2 Hz, 6.5 Hz), 4.22-4.13 (m, 1H), 3.87-3.81 (m, 1H), 3.77 (s, 1H), 3.52-3.45 (m, 1H), 3.29-3.20 (m, 1H), 2.52 (dd, 1H, J=3.0 Hz, 11.5 Hz), 2.44 (dd, 1H, J=3.7 Hz, 13.2 Hz), 2.21 (dd, 1H, J=7.1 Hz, 13.2 Hz), 2.02-1.78 (m, 5H), 1.78-1.61 (m, 5H), 1.60-1.41 (m, 5H), 1.31 (dd, 1H, J=4.2 Hz, 12.6 Hz), 1.24 (d, 6H, J=2.5 Hz), 1.19 (d, 1H, J=6.0 Hz), 0.88-0.87 (m, 18H), 0.52 (s, 1H), 0.07-0.06 (m, 12H).

Example 7: Preparation of Compound of Formula (1)

The compound of formula (10) (23.94 g, 36.99 mmol) in which the solvent was completely dried was dissolved in tetrahydrofuran (23.9 mL, 1 v/w) under argon gas, and 1M of tetrabutylammonium fluoride tetrahydrofuran solution (185.0 mL, 185.00 mmol) was added thereto at 20 to 25° C., followed by stirring at the same temperature for 72 hours. 10% of ammonium chloride aqueous solution (300 mL, 12.53 v/w) and ethyl acetate (100 mL, 4.18 v/w) were added to the resulting solution to separate layers, and the organic layer was obtained. Ethyl acetate (300 mL, 12.53 v/w) was added to the aqueous layer to extract twice. The combined organic layer was dried over sodium sulfate, followed by filtration and concentration. The residue was purified by column chromatography (dichloromethane:acetonitrile=2:1) to give the compound of formula (1) (15.42 g, 94%). The obtained compound of formula (1) was recrystallized (hexane:ethyl acetate=40:9) to give the compound of formula (1) (11.34 g, 74%) which is a purified crystalline solid.

$^1$H NMR (300 MHz, CDCl$_3$) δ 6.35 (d, 1H, J=11.2 Hz), 6.03 (d, 1H, J=11.3 Hz), 5.32 (m, 1H), 4.98 (m, 1H), 4.42 (m, 1H), 4.21 (m, 1H), 3.87-3.81 (m, 2H), 3.51-3.44 (m, 1H), 3.30-3.22 (m, 1H), 2.83 (dd, 1H, J=3.3 Hz, 11.8 Hz), 2.58 (dd, 1H, J=3.4 Hz, 13.4 Hz), 2.30 (dd, 1H, J=6.6 Hz, 13.4 Hz), 2.18-2.16 (m, 1H), 2.04 (m, 1H), 2.04-1.85 (m, 5H), 1.73 (d, 1H, J=5.6 Hz), 1.69-1.44 (m, 7H), 1.31 (dd, 1H, J=3.9 Hz, 12.7 Hz), 1.23 (s, 6H), 1.19 (d, 3H, J=6.0 Hz), 0.53 (s, 3H); $^{13}$C NMR (75 MHz, CDCl$_3$) M47.7, 142.1, 133.5, 124.6, 117.5, 111.9, 78.7, 70.7, 70.6, 66.7, 65.5, 57.1, 56.1, 45.2, 44.8, 42.8, 41.5, 39.5, 29.2, 29.1, 28.9, 25.6, 23.2, 22.2, 18.9, 12.6.

The invention claimed is:

1. A process for preparing a compound of the following formula (5), which comprises the steps of:
   (i) subjecting a compound of the following formula (2) to ozonolysis and reduction to obtain a compound of the following formula (3);
   (ii) subjecting the compound of the following formula (3) to Baeyer-Villiger oxidation to obtain a compound of the following formula (4); and
   (iii) subjecting the compound of the following formula (4) to Horner-Wadsworth-Emmons reaction with a compound of the following formula (6) to provide the compound of the following formula (5):

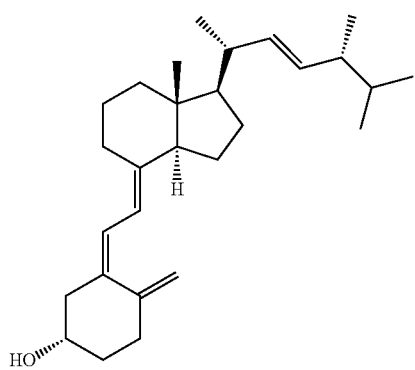
(2)

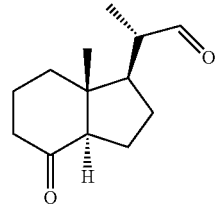
(3)

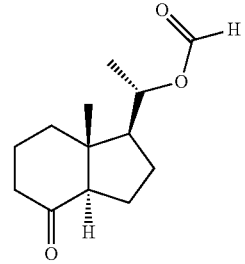
(4)

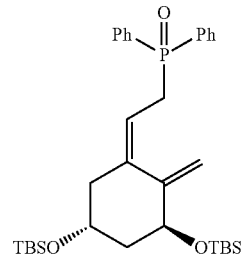
(6)

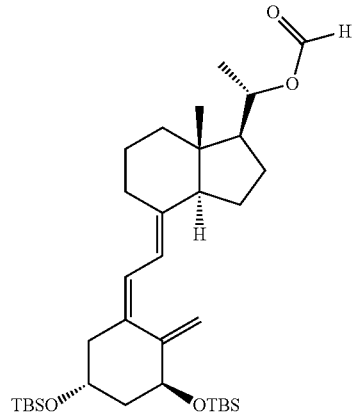
(5)

wherein

TBS is t-butyldimethylsilyl, and

Ph is phenyl.

2. The process according to claim 1, wherein the ozonolysis of step (i) is carried out using ozone in the presence of a base.

3. The process according to claim 1, wherein the Baeyer-Villiger oxidation of step (ii) is carried out using performic acid.

4. The process according to claim 1, wherein the Horner-Wadsworth-Emmons reaction of step (iii) is carried out in the presence of a base.

5. A compound of the following formula (5):

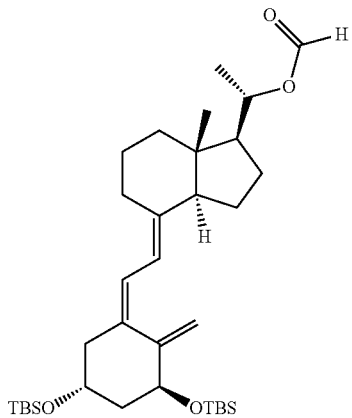
(5)

wherein

TBS is t-butyldimethylsilyl.

6. A process for preparing maxacalcitol of the following formula (1), which comprises the steps of:
- (iv) subjecting a formate group of a compound of the following formula (5) to hydrolysis to obtain a compound of the following formula (7);
- (v) subjecting the compound of the following formula (7) to nucleophilic substitution with a compound of the following formula (8) to obtain a compound of the following formula (9);
- (vi) subjecting an epoxide group of the compound of the following formula (9) to ring-opening reduction to obtain a compound of the following formula (10); and
- (vii) deprotecting a t-butyldimethylsilyl protecting group of the compound of the following formula (10) to provide the compound of the following formula (1):

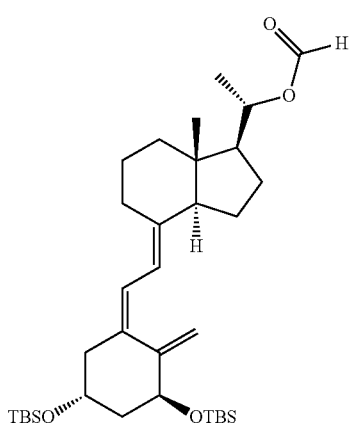
(5)

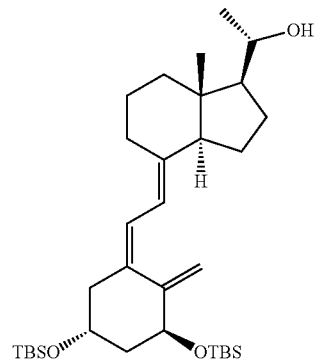
(7)

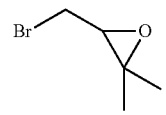
(8)

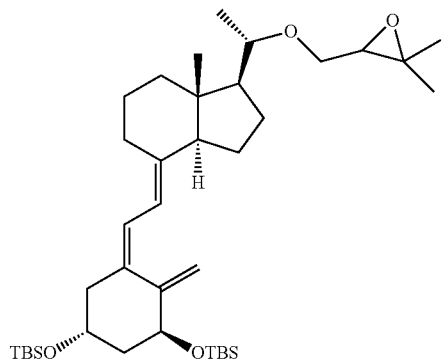
(9)

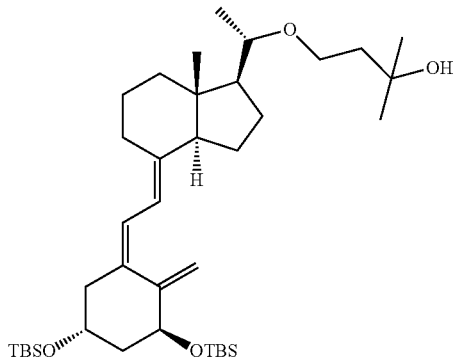
(10)

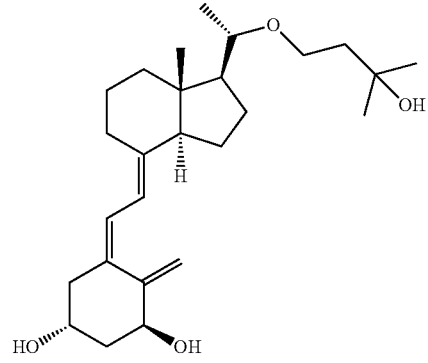
(1)

wherein,

TBS is t-butyldimethylsilyl.

7. The process according to claim 6, wherein the hydrolysis of step (iv) is carried out in the presence of a base.

8. The process according to claim 6, wherein the nucleophilic substitution of step (v) is carried out in the presence of a base.

9. The process according to claim 6, wherein the ring-opening reduction of step (vi) is carried out using Li[(CH$_3$CH$_2$CH(CH$_3$)$_3$BH].

10. The process according to claim 6, wherein the deprotection of step (vii) is carried out in the presence of a fluoride compound.

\* \* \* \* \*